United States Patent [19]
Pakhomov et al.

[11] 4,415,550
[45] Nov. 15, 1983

[54] TREATMENT-AND-PROPHYLACTIC TOOTH PASTE POSSESSING ANTICARIOUS EFFECT

[76] Inventors: Gennady N. Pakhomov, Leninsky prospekt 123/1, kv. 529, Moscow; Anita Y. Luste, ulitsa Lachplesha 27, kv. 22; Galina I. Kadnikova, ulitsa Ya. Rudzutaka 60, kv. 10, both of Riga; Analy G. Kolesnik, ulitsa Shosseinaya, 58, korpus 2, kv. 59, Moscow; Lidia N. Lubotskaya, ulitsa Maskavas 108/110, kv. 4, Riga; Rita M. Plyavniestse, "Plyavnieki", Rizhsky raion p/o "Katlakalns"; Jury A. Tarasenko, ulitsa Dzirtsiema 43, kv. 9, Riga, all of U.S.S.R.; deceased Konstantinov, late of Riga, U.S.S.R., by Aina R. Sils, administrator

[21] Appl. No.: 472,227

[22] Filed: Mar. 4, 1983

[51] Int. Cl.$^3$ .................. A61K 7/18; A61K 33/16; A61K 35/32
[52] U.S. Cl. .................... 424/57; 424/49; 424/52; 424/95; 424/151
[58] Field of Search .................. 424/49–58, 424/95, 151

[56] References Cited

U.S. PATENT DOCUMENTS

| 1,664,182 | 3/1928 | Parisi | 424/95 |
| 2,154,168 | 4/1939 | Klein et al. | 424/57 |
| 2,968,593 | 1/1961 | Rapkin | 424/95 |
| 3,743,721 | 7/1973 | Mattox | 424/95 |
| 4,172,128 | 10/1979 | Thiele et al. | 424/95 |
| 4,327,079 | 4/1982 | Aoki | 424/57 |
| 4,342,741 | 8/1982 | Aoki | 424/57 |
| 4,357,317 | 11/1982 | Weyn et al. | 424/52 |

FOREIGN PATENT DOCUMENTS 674909  7/1952  United Kingdom ............... 424/95

Primary Examiner—Shep K. Rose
Attorney, Agent, or Firm—Burgess, Ryan & Wayne

[57] ABSTRACT

A treatment-and-prophylactic tooth paste possessing anticarious effect which comprises an abrasive agent, a gellating agent, a wetting agent, a surfactant, a flavouring agent, 0.5 to 2% by weight of an anticarious substance which is a product obtained by treatment of bone tissue with a diluted mineral acid to a complete dissolution of mineral components and water-soluble proteins contained in the bone tissue, separation of the resulting solution, dilution thereof with water with the addition of a stabilizing agent, citric acid or salts thereof, followed by neutralization of the solution and drying, which contains the following components, percent by weight:

| calcium | 2 to 6 |
|---|---|
| sodium | 19 to 23 |
| potassium | 0.04 to 0.18 |
| mineral acid anion | 6 to 10.6 |
| orthophosphoric acid anion | 1.5 to 5.0 |
| water-soluble proteins | 1.0 to 5.0 |
| magnesium | 0.05 to 0.2 |
| a mixture of trace elements including fluorine, manganese, tin, zinc, iron | 0.01 to 0.02 |
| complex citrate compounds as calculated for citric acid anion | the balance. |

4 Claims, No Drawings

TREATMENT-AND-PROPHYLACTIC TOOTH PASTE POSSESSING ANTICARIOUS EFFECT

FIELD OF THE INVENTION

The present invention relates to stomatology and, more specifically, to a treatment-and-prophylactic tooth paste possessing anticarious effect adapted for everyday hygiene of the oral cavity and for providing antiinflammatory effect in the case of periodontal diseases and anesthetic effect in the case of hyperesthesia of hard dental tissues.

Caries is the important problem of stomatology, since 90 percent of population suffer from it. It causes grave effects: inflammatory processes in the dento-maxillary system, diseases of the gastro-intestinal tract, disturbances of the organism reactivity and allergization, chronic septicemia.

BACKGROUND OF THE INVENTION

Known in the art are various treatment-and-prophylactic tooth pastes possessing anticarious effect and comprising an abrasive agent, a gelating agent, a wetting agent, a surfactant, a preservative, a sweetening agent, a flavouring agent and substances providing an anticarious effect. For example, known is a treatment-and-prophylactic tooth paste possessing anticarious effect which has the following composition, percent by weight:

| | |
|---|---|
| abrasive agent with the particle size of 15μ (silica with a coating of curable diallylphthalate) | 25.0 |
| glycerol | 30.0 |
| tin fluoride | 0.4 |
| hydroxyethylcellulose | 1.5 |
| laurylethylenoxide | 1.0 |
| sweetening agent (saccharin) | 0.2 |
| flavouring substances | 0.9 |
| water | 41.0 |

(cf. L. Chalmers, Soap, Perfumery and Cosmetics, 1971, No. 119, 716-726, 728-734).

Also known is a treatment-and-prophylactic tooth paste possessing anticarious effect which contains an aqueous wetting vehicle with dissolved therein calcium ions in the amount of not less than 50 ppm and a source of phosphate ions in the amount of not less than 50 ppm. The ratio of calcium ions to phosphate ions is 0.01–100:1. Furthermore, this tooth paste contains a gelating agent, a compound liberating an anticarious agent-fluoride, and an acid or its perorally administrable water-soluble salt: diaminetetramethylenephosphonic acid of the formula $(M_2O_3PH_2C)_2N(CH_2)_nN(CH_3PO_3M_2)_2$ where $n=1-10$, phosphonoacetic acid or a salt thereof of the given formula $M_2O_3PCH_3COOM$ peroxydiphopshate of the formula $M_4P_2O_8$, an oligomer of the formula:

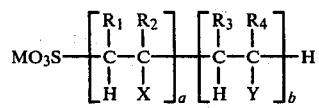

wherein M is hydrogen or perorally administrable cation; $R_1$–$R_4$—hydrogen, methyl or ethyl; Y—hydrophilic group—COOM, $CONH_2$ or $CH_2OH$; X—hydrophobic group——CN, COOR, —$COOR_5OR$, —CONHR or —$COONHR_5COR$, R—$C_1$–$C_8$—alkyl, $R_5$—$C_1$–$C_4$—alkylene, $a=0-7$, and $a+b=4-15$. The paste has a pH value within the range of from 5 to 9 (cf. U.S. Pat. No. 4,177,258 published 4.12.79).

Also known in the art is a treatment-and-prophylactic tooth paste possessing anticarious effect which has the following composition, percent by weight:

| | |
|---|---|
| glycerol | 25.0 |
| sodium salt of carboxymethylcellulose | 1.0 |
| sodium fluoride | 0.17 |
| monosubstituted sodium fluorophosphate | 0.17 |
| sodium laurylphosphate | 1.5 |
| saccharin | 0.2 |
| calcium dioxide | 45.0 |
| $CaSiO_3$ | 1.0 |
| flavouring substance | 1.0 |
| water | the balance |

(cf. British Patent No. 1,435,624 published 12.05.1976).

The above-discussed treatment-and-prophylactic prior art tooth pastes possessing anticarious effect feature a low level of the latter due to the fact that the use of fluorides fails to ensure a sufficient resistance of teeth to caries.

SUMMARY OF THE INVENTION

It is the main object of the present invention to provide a tooth paste which would have a highly pronounced anticarious effect.

It is another object of the present invention to provide a tooth paste possessing antiinflammatory and anesthetic effects and having a pleasant taste, high foaming and refreshing properties.

The main and other objects of the present invention are accomplished by that the treatment-and-prophylactic tooth paste possessing anticarious effect and comprising an abrasive agent, a gelating agent, a wetting agent, a surfactant, a flavouring agent, and an anticarious substance contains, according to the present invention, as the anticarious substance, 0.5 to 2% by weight of a product obtained by treatment of a bone tissue by a dilute mineral acid untill a complete dissolution of mineral components and water-soluble proteins contained in the bone tissue, takes place separation of the resulting solution, dilution thereof with water with the addition of a stabilizing agent-citric acid or salts thereof, followed by neutralization of the solution and drying, and containing the following components, percent by weight:

| | |
|---|---|
| calcium | 2 to 6 |
| sodium | 19 to 23 |
| potassium | 0.04 to 0.18 |
| mineral acid anion | 6 to 10.6 |
| orthophosphoric acid anion | 1.5 to 5.0 |
| water-soluble proteins | 1.0 to 5.0 |
| magnesium | 0.05 to 0.2 |
| a mixture of trace elements including fluorine, manganese, tin, zinc, iron | 0.01 to 0.02 |
| complex citrate compounds as calculated for citric acid anion | the balance. |

It is preferred to use, as the treatment-and-prophylactic tooth paste possessing anticarious effect, a paste containing a preservative in addition to the above-mentioned components in the following proportions thereof, percent by weight:

| | |
|---|---|
| abrasive agent | 34 to 42.5 |
| gelating agent | 19 to 25 |
| wetting agent | 0.8 to 1.4 |
| surfactant | 1.5 to 2.6 |
| preservative | 0.18 to 0.22 |
| flavouring agent | 0.8 to 1.2 |
| anticarious substance | 0.5–2.0 |
| water | the balance. |

It is also preferred to use a treatment-and-prophylactic tooth paste possessing anticarious effect which has the following composition, percent by weight:

| | |
|---|---|
| sodium salt of carboxymethylcellulose | 0.97–1.10 |
| glycerol | 19.0–21.00 |
| sodium benzoate | 0.19 to 0.21 |
| anticarious substance | 1.00 to 2.00 |
| dicalcium phosphate dihydrate | 34.00 to 38.00 |
| chalk | 4.00 to 4.50 |
| sodium laurylphosphate | 2.50 to 2.60 |
| flavouring substance | 0.80 to 1.20 |
| water | the balance. |

To impart glass to the tooth paste and avoid stratification thereof, the tooth paste composition additionally incorporates a high-purity petroleum oil with a kinematic viscosity of $16.5 \times 10^{-6}$ to $23.0 \times 10^{-6}$ m$^2$/sec at the temperature of 50° C., a buffer solution with a pH of from 8 to 10 and silica with a particle size of 5–20 nm with the content of SiO$_2$ of 99.8% at the following proportions of the starting components, percent by weight:

| | |
|---|---|
| chalk | 34 to 40 |
| glycerol | 21 to 25 |
| sodium salt of carboxymethylcellulose | 0.8 to 1.4 |
| high-purity petroleum oil with the kinematic viscosity of $16.5 \times 10^{-6}$ to $23.0 \times 10^{-6}$ m$^2$/sec at the temperature of 50° C. | 0.5 to 1.5 |
| sodium laurylsulphate | 1.5 to 2.5 |
| sodium benzoate | 0.18 to 0.22 |
| saccharin | 0.04 to 0.08 |
| flavouring agent | 0.8 to 1.2 |
| buffer solution with pH = 8–10 | 2.5 to 3.5 |
| silica with a particle size of 5–20 nm and the content of SiO$_2$ of 99.8% | 1.5–2.5 |
| anticarious substance | 0.5 to 1.5 |
| water | the balance. |

DETAILED DESCRIPTION OF THE INVENTION

The tooth paste according to the present invention has a high level of the anticarious effect owing to the mechanism of its action different from that of fluorine preparations. The macro- and trace elements contained in the paste of this invention are in the ionized state and, upon application of the solution onto the dental surface, they cause substitutions in an elementary cell of enamel crystals or form new crystals. This mechanism of action results in an increased resistance of sound teeth against caries, while at the initial stages of caries-in an enhanced remineralization process.

The tooth paste according to the present invention has clearly pronounced antiinflammatory properties. Its use in the cases of periodontal diseases (including gingivitis) facilitates normalization of gingiva tissues (decreased odontorrhagia, edema and pastosity of gingival papillae). Furthermore, the tooth paste according to the present invention has a dinstinct anesthetic effect. Its application eliminates a hypersensitivity of teeth in areas of various non-caries injuries (erosions, necrosis, wedge-shaped defects), as well as hyperesthesia of dentine of bare necks of tooth roots at periodontal disease. The paste has a stable neutral reaction (pH=7.8–8.0), contains no pathogenic microflora and possesses bacteriostatic and fungicidal properties. As to its appearance, the tooth paste according to the present invention comprises a white glossy uniform paste-like mass without grains, with a pleasant taste and odour retained unchanged during storage, easily squeezed out of tubes and not spread out when applied onto a tooth brush (dynamic viscosity limit point—1,500–4,000 dyne/cm$^2$; plasticity coefficient—20 to 75).

The paste according to the present invention has high foaming and refreshing properties (foam number is of 250 to 350 ml, foam stability of 0.8 to 1.0) as well as good cleaning properties which is demonstrated by statistically true reduction of oral hygiene index (OHI-S).

The paste according to the present invention and the anticarious substance incorporated therein have been tested experimentally on animals and in clinics on patients. A 3% solution of the anticarious substance was tested in comparison with control. The tests were carried out on 80 Wistar rats of one month's age (40 rats for the test solution and 40—for the control group). All the animals were set on the cariogenic Stephan-580 diet and during 4 weeks of the experiment the test solutions were daily applied onto teeth for 3 minutes. On completion of the experiment the teeth were extracted and the carious index was determined following a generally-accepted procedure. The results obtained in these experiments are shown in Table 1 hereinbelow.

TABLE 1

Comparative data on anticarious efficiency of the solution of the anticarious compound according to the present invention and the control

| | Characteristics | | | | | |
|---|---|---|---|---|---|---|
| | Fissures | | Contact zones | | Total in all zones | |
| Preparation (group) | Carious index | Anticarious efficiency, % | Carious index | Anticarious efficiency, % | Anticarious index | Carious efficiency, % |
| Control group | 26.75 | — | 2.76 | — | 29.51 | — |
| Solution of the anticarious substance of the invention | 20.42 | 23.7 | 1.00 | 63.7 | 21.42 | 27.4 |

The caries-preventive efficiency of the anticarious substance according to the present invention in the form of a 3% solution for applications when used for not less than 1.5 years with the administration schedule of 2 times a month on children aged 7–10 years is, as regarded by the characteristic of a relative reduction of the DMF-T index increment, 44.1 to 53.7 percent, according to DMF-S index—from 40.2 to 58.0%; according to the data of CRT-test the acid resistance of the enamel is considerably increased.

The efficiency of a 3% solution of the anticarious substance in the treatment of early stages of dental caries is high; the positive effect of the treatment—disappearance or reduction of demineralization spots is observed in 72.4–84%, stabilization of the process in 14–31.9%, the absence of therapeutic effect—in 2–8% of the cases.

The efficiency of a 3% solution of the anticarious substance in the treatment of hyperesthesia of hard dental tissues is good; fully increased sensitivity of tooth necks is eliminated in 23.2–36.4% of the cases.

Clinical tests of the anticarious substance were carried out with the view to study its preventive effect on children and pregnant women, as well as to study its efficiency in the conservative treatment of focal demineralizations of dental enamel. The anticarious substance was used in the form of a 1.5–3% solution for applications.

In accordance with the results of epidemiological studies 176 children aged 7–8 years were chosen. The children were divided into two groups:

Group I—children to whom the anticarious solution was administered by application—81 persons;

Group II—control group of children—95 persons.

The application of the solution was effected after a preliminary tooth brushing with a hygienic tooth paste. Then the teeth were isolated from saliva by means of lignin insertions and dried by air jet. The solution was applied on all the surfaces of the teeth by means of spoons made of a flexible plastic, whereinto abundantly wetted cotton wool tampons were placed. The application duration was 10 minutes for each jaw. After applications, the children were advised to abstain from taking meals and drinking for 2 hours. All subsequent applications were conducted following these procedure one every two weeks.

After the primary examination of the mouth cavity there was noticed a relatively uniform level of caries attack reaching values of 1.12±0.13 to 1.30±0.13 according to DMF-T.

The results of application of the anticarious solution are shown in Table 2.

It is seen from the Table that the reduction in caries increment in Group I of children was 44.7 and 49.5% respectively based on DMF-T and DMF-S.

In the analysis of the cariostatic effect of the test substance relative to certain groups of teeth, its effect was established on already erupted first molars and on incisors erupted during the observation period.

The solution of the test substance was used for the treatment of demineralization of teeth in 81 schoolchildren aged 7 to 14 years.

The children were divided into two subgroups depending on the demineralization form:

Group 3a—children with slowly progressing demineralization (42 schoolchildren altogether);

Group 3b—children with rapidly progressing demineralization (39 schoolchildren altogether).

On the whole, demineralization was noted on 229 teeth of the children of Group 3a and 248 teeth of children of Group 3b (see Table 3). The control groups were the same as in the previous experiment designated in the Table as Groups 1a and 1b.

To attain a positive result in the treatment of teeth with the solution of the test substance, it was necessary to carry out 10–15 applications in Group 3a (on the average) and 20–25 applications—in Group 3b.

The remineralizing therapy was more efficient in the treatment of the slowly-progressing demineralization process. The spots of a small size (2 and 2–3 $mm^2$) reduced and disappeared faster than the larger-size lesions. The conservative treatment of the rapidly-progressing demineralization of the children's teeth of Group 3b was less efficient, though the direct relationship of the treatment efficiency vs. the spot size was noticed in this group as well (see Table 4).

The positive treatment—disappearance of spots in Group 3a was observed on 193 teeth out of 229 (84%±2,4) as compared to the control group where the positive treatment result was noted on only 100 teeth out of 270 (36%±2.9).

The stabilization process was noted in Group 3a on 31 teeth (14%±6.23) and 87 teeth (31%±2.8) in the control group.

Increase of spots and formation of cavities in Group 3a was noted on only 5 teeth out of 229 (2±0.9%), while in the control Group—on 92 out of 279 (33±2.8%).

The difference between the characteristics of Group 3a and the control Group 1a is statistically significant (See Table 4).

In Group 3b the treatment of rapidly-progressing demineralization gave a positive result on 155 teeth out of 248 (63%±3.0), whereas in the control group spontaneous disappearance was noted on 33 teeth out of 305 which was only 11%±1.8. On 60 teeth of children of Group 3b (24%±2.7) the process was stabilized. In the demineralization foci on 33 teeth of children of Group 3b, cavities were formed.

The difference between the characteristics of Group 3b and the Control group 1b is statistically significant. (See Table 4).

Therefore, the average positive result in the treatment of rapidly- and slowly-progressing demineralization of dental enamel is 73.5%.

The solution of the substance possessing anticarious effect according to the present invention was tested on pregnant women. From the epidemiological studies on pregnant women it was found that with extension of the pregnancy period the frequency and intensity of focal demineralizations of dental enamel were increased. To carry out preventive measures against these phenomena, on 69 (Group I) pregnant women the solution of the anticarious substance according to the present invention was used in the form of applications. 64 pregnant women formed the control group (Group II).

TABLE 2

| | | | | Characteristics after 1 year of observation | | | | Characteristics after 3 years of observation | | | | |
|---|---|---|---|---|---|---|---|---|---|---|---|---|
| Nos 1 | Group No. 2 | Preventive measures 3 | Number of examined patients 4 | Caries increment | | Reduction of increment, % | | Number of examined patients 9 | Caries increment | | Reduction of increment, % | |
| | | | | DMF-T 5 | DMF-S 6 | DMF-T 7 | DMF-D 8 | | DMF-T 10 | DMF-S 11 | DMF-T 12 | DMF-S 13 |
| 2 | I | Application of the re-mineralizing solution of the | 81 | 0.78 ± 0.16 | 1.12 ± 0.28 | 19.6 | 22.7 | 81 | 1.61 ± 0.18 | 2,59 ± 0.34 | 44.7 | 49.5 |

TABLE 2-continued

| | | | Characteristics after 1 year of observation | | | | | Characteristics after 3 years of observation | | | | |
|---|---|---|---|---|---|---|---|---|---|---|---|---|
| | | | Number of examined patients | Caries increment | | Reduction of increment, % | | Number of examined patients | Caries increment | | Reduction of increment, % | |
| Nos | Group No. | Preventive measures | | DMF-T | DMF-S | DMF-T | DMF-D | | DMF-T | DMF-S | DMF-T | DMF-S |
| 1 | 2 | 3 | 4 | 5 | 6 | 7 | 8 | 9 | 10 | 11 | 12 | 13 |
| 3 | II | test substance on teeth Control | 95 | 0.97 ± 0.14 | 1.45 ± 0.24 | — | — | 78 | 2.91 ± 0.16 | 5.13 ± 0.25 | — | — |

TABLE 3

Number of teeth of Group 3 and Group I (control) with demineralization foci according to their size

| Spot size | Number of teeth with demineralization foci | | | |
|---|---|---|---|---|
| | 1a Control group | 1b Control group | Group 3a | Group 3b |
| 2 mm² | 73 | 48 | 81 | 24 |
| 2–3 mm² | 125 | 102 | 117 | 120 |
| 3 mm² | 81 | 155 | 31 | 104 |
| Total number of spots | 279 | 305 | 229 | 248 |

The studies of both groups of women (1–3 months of pregnancy) revealed a comparatively similar level of injury of teeth by focal demineralizations—29–30% with an average injury of 1.8±0.3 teeth.

By the end of pregnancy the focal demineralizations of dental enamel in the control group women were in 64% of the cases with an average characteristic of 5.23± ±0.7 teeth.

The use of the substance possessing anticarious effect according to the present invention on women of Group I made it possible to not only prevent the formation of novel focal lesions of enamel, but also to stabilize the process in already existing foci (no increase of the demineralization foci or formation of cavities was observed).

and the carious index was determined following the generally-accepted procedure. Also studied was the anticarious activity (efficiency) of remineralizing preparations expressed as percentage of carious index reduction in test groups as compared to the control group. The results thus obtained are given in Table 5, hereinbelow.

The results of microscopic analyses of jaws' half-sections of the control group of rats showed a high degree of caries attack which demonstrated a successful reproduction of a model analog of the carious process suitable for the study of anticarious effectiveness of preparations. Tooth cleaning with the placebo-paste provided an insignificant anticarious effect at early stages of caries development. The paste according to the present invention had an increased anticarious effect. The carious index in rats was reduced by 31.0%.

For a detailed study of the mechanism of action of the preparation, the analysis of injury of fissures and contact zones of rat's molars was performed. After tooth brushing with the placebo-paste the fissures carious index was 31.21 and its reduction was 9% as compared to the control; in the case of the paste according to the present invention these parameters were 24.4 and 26.0% respectively.

Relative to its action on the contact zones, the preparation according to the present invention had the effect

TABLE 4

Results of the treatment of children's teeth by the remineralizing solution of the test substance possessing anticarious effect

| | | Characteristic of demineralization foci | | | | | | | | | | |
|---|---|---|---|---|---|---|---|---|---|---|---|---|
| | Result of the treatment of demineralization of teeth | Spot distribution in children of Group 3a | | | | | | Spot distribution on children of Group 3b | | | | |
| | | According to size | | | According to number | | t relative to the control (p < 0.001) | According to size | | | According to number | | t relative to the control (p < 0.001) |
| Nos | | <2 mm² | 2–3 mm² | >3 mm² | Abs. | M ± m, % | | <2 mm² | 2–3 mm² | >3 mm² | Abs. | M ± m, % | |
| 1 | 2 | 3 | 4 | 5 | 6 | 7 | 8 | 9 | 10 | 11 | 12 | 13 | 14 |
| 2 | Disappearance of spots | 64 | 98 | 31 | 193 | 84 ± 2.4 | 10.8 | 19 | 73 | 63 | 255 | 63 ± 3.0 | 12.8 |
| 3 | Stabilization of the process | 13 | 18 | — | 31 | 14 ± 2.3 | 4.5 | 1 | 31 | 23 | 60 | 24 ± 2.7 | 3.4 |
| 4 | Formation of defects | 4 | 1 | — | 5 | 2 ± 0.9 | 8.9 | 4 | 16 | 13 | 33 | 13 ± 2.1 | 14.7 |
| 5 | Total | | | | 229 | 100 | | | | | 248 | 100 | |

The tooth paste according to the present invention was subjected to testing. The tooth paste according to the present invention, as well as a placebo-paste were tested on 90 Wistar rats aged one month (30 rats for each type of paste and 30—control group). All animals were fed with the cariogenic Stephan-580 diet and during 4 weeks of the experiments their teeth were cleaned by specially made brush for 1.5 minute on each jaw. On completion of the experiment the teeth were extracted by 1.6 times higher than that of the placebo-paste.

Clinical tests of the tooth paste according to the present invention and the placebo-paste were performed on 283 children of the starting age of 7–8 years for the period of three years. The tooth cleaning was effected in the following order: upper right chewing surfaces, upper left chewing surfaces; lower right and lower left chewing surfaces; right cheek and left cheek surfaces of the upper and lower jaw (except for the front teeth); upper lip surfaces, lower lip surfaces of all incisors; upper lingual surfaces of incisors. The cleaning duration was 3 minutes. The caries-preventive activity was evaluated by comparison of DMF of teeth (DMF-T) and surfaces (DMF-S) indeces and their increments between the first and subsequent control examinations one year and three years after the beginning of observation. The results of the prophylactic effect of the tooth paste according to the present invention were also studied in the analysis of attack of all surfaces of the first permanent molar of both the control and test groups. Antiinflammatory and cleaning properties of the tooth paste according to the present invention were also studied. The results obtained in these tests are shown in Tables 6, 7, 8, 9 and 10 hereinbelow.

TABLE 5

Comparative data on anticarious efficiency of the tooth paste according to the present invention and placebo-paste

| Nos | Preparation (group) | Characteristics | | | | | |
|---|---|---|---|---|---|---|---|
| | | Fissures | | Contact zones | | Total in all zones | |
| | | Carious index | Anticarious efficiency, % | Carious index | Anticarious efficiency, % | Carious index | Anticarious efficiency, % |
| 1 | 2 | 3 | 4 | 5 | 6 | 7 | 8 |
| 2 | Control | 33.2 | — | 8.65 | — | 41.87 | — |
| 3 | Placebo-paste | 31.21 | 9.0 | 5.51 | 3.6 | 36.72 | 12.6 |
| 4 | Paste of the present invention | 24.38 | 26.6 | 3.36 | 4.4 | 28.88 | 31 |

The use of the tooth paste according to the present invention for three years resulted in reduction of the degree of teeth injury with caries, as compared to the control group, by 1.5 times according to DMF-T index and by 1.8 times according to DMF-S index, while as compared to the tooth paste of a known composition—by 1.27 time according to DMF-T and by 1.34 time according to DMF-S indeces.

The reduction of caries after the use of the tooth paste according to the present invention was 37.8% (DMF-T) and 47% (DMF-S), whereas the regular use of the placebo-paste ensured reduction of caries only by 7.1% according to DMF-T and by 16.2% according to DMF-S indeces.

The analysis of the cariostatic effect of the paste of this invention relative to individual groups of teeth revealed its effect on both already erupted, by the beginning of the experiment, first molars, and on incisors which erupted during the period of observation.

In the analysis of the data of the first examination it was found (see Table 8) that caries injured mainly chewing surfaces, and in all groups similarly both in respect to chewing and other surfaces. After 3 years of observation there was established an increased injury of all surfaces of the first molars with caries.

The caries increase at circumneck surfaces (Table 9) showed no essential difference between the effect produced by the placebo-paste and the tooth paste according to the present invention, which can be due to a high cleaning ability of the placebo-paste; regular and proper care of the oral cavity contributes to preventing dental deposits and saliva in this area exerts its mineralizing effect to a greater extent.

The increment of dental caries of the chewing surfaces in the group of children who cleaned their teeth by the tooth paste according to the present invention was 1.16± ±0.23 at the reduction of caries increment of 42.8%; after application of the placebo-paste the increment was 1.74± ±0.15, reduction—only 14.3%.

The use of the placebo-paste reduced the caries attack of approximal surfaces by 2.8%, whereas the use of the tooth paste according to the present invention—by 34.8% (Table 9).

After the 3-years' period of use of the paste according to the present invention a similar hygienic effect was observed (see Table 10), hygiene index (OHI-S) was the same, but the PMA-index (inflammation index) was significantly lesser not only in comparison with the control group of children but with the group of children who cleaned their teeth with the placebo-paste. This enables a conclusion to be made that pastes of such type contribute to improve blood circulation, enhancing metabolism, outflow of the tissue liquid from the inflamed gingiva.

The tooth paste according to the present invention was also subjected to experimental and microbiological tests.

TABLE 6

Dynamics of DMF-T and DMF-S indeces in the examined groups of children during the observation period

| Nos | Group No. | Preventive measures | Prior to the use of the preparation /1st examination/ | | | After 1 year of observation /2nd examination/ | | | After 3 years of observation /3rd examination/ | | |
|---|---|---|---|---|---|---|---|---|---|---|---|
| | | | Number of examined children | DMF-T | DMF-S | Number of examined children | DMF-T | DMF-S | Number of examined children | DMF-T | DMF-S |
| 1 | 2 | 3 | 4 | 5 | 6 | 7 | 8 | 9 | 10 | 11 | 12 |
| 2 | I | Control | 106 | 1.30 ± 0.13 | 1.70 ± 0.20 | 96 | 2.27 ± 0.16 | 3.15 ± 0.29 | 78 | 4.21 ± 0.20 | 6.83 ± 0.44 |
| 3 | II | Tooth-cleaning with the placebo-paste | 93 | 1.12 ± 0.13 | 1.44 ± 0.21 | 87 | 2.17 ± 0.16 | 3.07 ± 0.27 | 83 | 3.82 ± 0.21 | 5.74 ± 0.46 |
| 4 | III | Tooth cleaning with the paste of the present invention | 95 | 1.19 ± 0.14 | 1.61 ± 0.21 | 89 | 2.09 ± 0.19 | 2.99 ± 0.34 | 89 | 3.00 ± 0.24 | 4.33 ± 0.43 |

TABLE 7

Dynamics of dental caries intensity during the observation period in examined groups of children

| | | Characteristics after 1 year of observation | | | | | Characteristics after 3 years of observation | | | | |
|---|---|---|---|---|---|---|---|---|---|---|---|
| | | Number of examined | Caries increment | | Reduction of increment caries, % | | Number of examined | Caries increment | | Reduction of caries increment, % | |
| Nos | Preventive measures | children | DMF-T | DMF-S | DMF-T | DMF-S | children | DMF-T | DMF-S | DMF-T | DMF-S |
| 1 | 2 | 3 | 4 | 5 | 6 | 7 | 8 | 9 | 10 | 11 | 12 |
| 2 | Control | 95 | 0.97 ± 0.14 | 1.45 ± 0.24 | — | — | 78 | 2.91 ± 0.16 | 5.13 ± 0.25 | — | — |
| 3 | Tooth cleaning with the placebo-paste | 87 | 1.05 ± 0.15 | 1.57 ± 0.24 | 8.2 | 8.3 | 83 | 2.70 ± 0.17 | 4.30 ± 0.26 | 7.1 | 16.7 |
| 4 | Tooth cleaning with the paste of the present invention | 89 | 0.90 ± 0.16 | 1.38 ± 0.28 | 7.2 | 4.8 | 89 | 1.81 ± 0.24 | 2.27 ± 0.35 | 37.8 | 47.0 |

TABLE 8

Distribution of the permanent first molar total DMF-S index, per examined patient, according to various surfaces in observed groups of children

| | | Results of first examination | | | | | Results of third examination | | | | |
|---|---|---|---|---|---|---|---|---|---|---|---|
| Nos | Group No. | Number of examined children | Circumneck surfaces | Chewing surfaces | Approximal surfaces | Total, all surfaces | Number of examined children | Circumneck surfaces | Chewing surfaces | Approximal surfaces | Total, all surfaces |
| 1 | 2 | 3 | 4 | 5 | 6 | 7 | 8 | 9 | 10 | 11 | 12 |
| 2 | I Control | 106 | 0.29 ± 0.06 | 1.20 ± 0.18 | 0.20 ± 0.05 | 1.69 ± 0.20 | 78 | 1.81 ± 0.24 | 3.23 ± 0.31 | 1.35 ± 0.17 | 5.76 ± 0.33 |
| 3 | II Tooth cleaning with the placebo-paste | 93 | 0.30 ± 0.06 | 0.94 ± 0.19 | 0.15 ± 0.04 | 1.39 ± 0.21 | 87 | 0.78 ± 0.17 | 2.68 ± 0.30 | 1.34 ± 0.22 | 4.80 ± 0.41 |
| 4 | III Tooth cleaning with the paste of the present invention | 95 | 0.24 ± 0.05 | 1.12 ± 0.19 | 0.21 ± 0.05 | 1.57 ± 0.21 | 89 | 0.62 ± 0.11 | 2.28 ± 0.25 | 0.96 ± 0.20 | 3.86 ± 0.34 |

TABLE 9

Distribution of the first molar total DMF-S index increment and its reduction for three years of observation according to various surfaces

| | | Characteristics | | | | | | | |
|---|---|---|---|---|---|---|---|---|---|
| | Character of | Circumneck surfaces | | Chewing surfaces | | Approximal surfaces | | Total of all surfaces | |
| Nos | preventive measures | Increment of DMF-S | Reduction, % | Increment of DMF-S | Reduction, % | Increment of DMF-S | Reduction, % | Increment of DMF-S | Reduction, % |
| 1 | 2 | 3 | 4 | 5 | 6 | 7 | 8 | 9 | 10 |
| 2 | I Control | 0.89 ± 0.09 | — | 2.03 ± 0.14 | — | 1.15 ± 0.11 | — | 4.07 ± 0.20 | — |
| 3 | II Tooth cleaning by the placebo paste | 0.48 ± 0.08 | 46.1 | 1.74 ± 0.15 | 14.3 | 1.19 ± 0.12 | 2.8 | 3.41 ± 0.21 | 16.2 |
| 4 | III Tooth cleaning by the paste of the present invention | 0.38 ± 0.12 | 57.3 | 1.16 ± 0.23 | 42.8 | 0.75 ± 0.15 | 34.8 | 2.29 ± 0.30 | 43.7 |

TABLE 10

Dynamics of hygienic characteristics in the observed groups

| | Characteristics of the first examination | | | Characteristics of second examination | | | Characteristics of third examination | | |
|---|---|---|---|---|---|---|---|---|---|
| Nos | Number of examined children | Inflammation index (PMA) | Hygiene index OHY-S | Number of examined children | Inflammation index (PMA) | Hygiene index OHI-S | Number of examined children | Inflammation index (PMA) | Hygiene index OHI-S |
| 1 | 2 | 3 | 4 | 5 | 6 | 7 | 8 | 9 | 10 |
| 2 | 106 | 2.5 ± 0.3 | 2.4 ± 0.2 | 95 | 3.0 ± 0.7 | 2.9 ± 0.3 | 78 | 3.1 ± 0.8 | 2.3 ± 0.2 |
| 3 | 93 | 2.4 ± 0.4 | 2.8 ± 0.3 | 87 | 2.3 ± 0.5 | 2.3 ± 0.5 | 83 | 1.8 ± 0.4 | 1.2 ± 0.1 |

TABLE 10-continued

| | Characteristics of the first examination | | | Dynamics of hygienic characteristics in the observed groups | | | | | |
|---|---|---|---|---|---|---|---|---|---|
| | | | | Characteristics of second examination | | | Characteristics of third examination | | |
| Nos 1 | Number of examined children 2 | Inflammation index (PMA) 3 | Hygiene index OHY-S 4 | Number of examined children 5 | Inflammation index (PMA) 6 | Hygiene index OHI-S 7 | Number of examined children 8 | Inflammation index (PMA) 9 | Hygiene index OHI-S 10 |
| 4 | 95 | 2.6 ± 0.3 | 2.4 ± 0.3 | 89 | 2.1 ± 0.6 | 1.3 ± 0.2 | 81 | 0.7 ± 0.3 | 1.1 ± 0.1 |

The result of microbiological testing of the tooth paste according to the present invention showed that inoculation of the paste onto different media revealed no pathogenic microflora in the paste. The paste possesses bacteriostatic effect the zone of retardation of the oral microflora growth is of 1.5 cm in diameter.

The experimental study was carried out for two months. The total number of examined persons was 163. Indications to administration of the tooth paste of the present invention were as follows:

inflammatory diseases of parodontium;

different forms of hyperesthesia of hard dental tissues observed at erosions of enamel, wedge-shaped defects, exposure of tooth necks in periodontal disease or after treatment of teeth before setting artificial crowns.

The effect of the tooth paste according to the present invention on to the oral mucous membrane, as well as its cleaning, refreshing and taste characteristics were preliminarily studied.

Subjected to observation were three groups of schoolchildren aged 7-8 years, each consisting of 30 children. Group I of schoolchildren was instructed to clean teeth with the paste according to the present invention; Group II—with a paste having similar composition but containing no active ingredient—i.e. anticarious substance; Group III of schoolchildren was control.

The children of Groups I and II cleaned their teeth under guidance of stomatologists for two months once a day at school during the large interval after breakfast. All the children were preliminarily taught how to clean teeth properly. The dynamics of oral hygiene and state of gingivae was evaluated by the results of four repeated examinations.

The results obtained were processes by the T-Student test of variation statistics. The difference between the initial and obtained data was evaluated by the t-coefficient. For the purpose of comparison of the effect produced by the paste according to the present invention and the control paste use was made of the criterion $^2$.

After 60 days of controlled tooth cleaning by schoolchildren their oral hygiene was substantially improved. The PMA-index characterizing the state of gingiva in schoolchildren of both groups remained without changes, i.e. no local irritative effect on the mucous membrane of gingiva was exerted by the tooth paste according to the present invention.

The majority of schoolchildren made a positive comment on the paste, specially mentioned its pleasant taste, good cleaning properties and a lasting refreshing effect.

No general side effects were obtained during the entire course of administration of the tooth paste according to the present invention.

The study of the antiinflammatory effect of the tooth paste of the present invention was carried out on 19 patients suffering from chronical catarrhal gingivitis. After 2 months' period of application of the tooth paste (with preliminary removal of dental calculus in all of the patients) in 16 patients normalization of gingivae was observed, in 3—diminished inflammatory phenomena, odontorrhagia, edema and pastosity of gingival papillae.

The study of the anesthetic effect of the tooth paste according to the present invention at (a) hyperesthesia of bare dental necks accompanying periodontal disease was carried out on 21 patients; (b) wedge-shaped defects—in 10 patients; (c) enamel erosions—in 6 patients; (d) at increased pain sensitivity of teeth after treatment thereof for artificial crowns—in 17 patients.

The procedure of the tooth paste application: usual tooth cleaning twice a day accompanied by a thorough rubbing of the paste into dental surfaces having increased pain sensitivity.

Hyperesthesia was considerably reduced or fully disappeared depending on the injury nature after 3–7 times of tooth cleaning. During the observation period the attained therapeutic effect was reliably stable.

The treatment-and-prophylactic tooth paste according to the present invention is an efficient preparation for prophylaxis and treatment of periodontal diseases and hyperesthesia of teeth.

The tooth paste according to the present invention is prepared by a conventional method. The gelating and wetting agents are mixed first. To the resulting gel-like mass all other components of the paste are added. To ensure a long-time storage of the paste, a preservative such as sodium benzoate is added thereto. To prevent stratification of the paste-like mass, it is added with a buffer solution with a pH of 8–10 and silica with a particle size of 5–20 nm and the content of $SiO_2$ of 99.8%. After the addition of each component the mixture is thoroughly agitated to obtain a uniform paste which is milled and packed.

The anticarious substance incorporated in the composition of the tooth paste according to the present invention is obtained in the following manner. A bone tissue is covered with a diluted mineral acid and kept therein under stirring until complete dissolution of mineral components and water-soluble proteins contained in the bone tissue occurred. Then the resulting solution is separated and diluted with water with the addition of a stabilizing agent-citric acid or salts thereof. Thereafter the solution is neutralized. To facilitate transportation and storage of the substance, it is obtained in the dry form. To this end, the solution is sprayed in a drier. The obtained product is a white amourphous powder having no odour, with a slightly salty taste, readily soluble in water, sparingly soluble in 95% alcohol, substantially insoluble in ether.

For a better understanding of the present invention, some specific examples illustrating compositions of the tooth paste possessing anticarious effect are given hereinbelow.

EXAMPLE 1

A treatment-and-prophylactic tooth paste possessing anticarious effect has the following composition, g:

| | | |
|---|---|---|
| glycerol | | 23.00 |
| sodium salt of carboxymethylcellulose | | 1.20 |
| sodium benzoate | | 0.20 |
| chalk | | 37.00 |
| carbonate buffer with pH = 9.0 | | 2.00 |
| silica with a particle size of 5-20 nm, the content of $SiO_2$ of 99.8% | | |
| anticarious substance of the following formulation, percent by weight: | | |
| calcium | 6.00 | |
| orthophosphoric acid anion | 5.00 | |
| sodium | 19.00 | |
| magnesium | 0.05 | |
| potassium | 0.04 | |
| mineral acid anion (chloride) | 6.00 | 1.00 |
| mixture of trace elements | 0.01 | |
| water-soluble proteins | 1.00 | |
| complex citrate compounds as calculated for citric acid anion | 63.90 | |
| saccharin | | 0.06 |
| sodium laurylsulphate | | 1.80 |
| high-purity petroleum oil with a kinematic viscosity of $16.5 \times 10^{-6}$–$23 \times 10^{-6}$ m²/sec at 50° C. | | 1.0 |
| flavouring agent | | 1.0 |
| water | | to 100 g. |

The tooth paste of this composition is prepared in the following manner. Glycerol and sodium salt of carboxymethylcellulose are intermixed. To the resulting gel-like mass all other components are added. After the addition of every component the mixture is thoroughly intermixed to obtain a uniform paste which is rolled and packed. The thus-obtained paste has the following properties:

| | |
|---|---|
| dynamic viscosity limit point | 3,400 dyne/cm² |
| plasticity coefficient | 70 |
| foam number | 350 ml |
| foam stability | 0.95 |
| a 30% aqueous solution of the paste suspension has pH = 9.0. | |

EXAMPLE 2

A treatment-and-prophylactic tooth paste possessing anticarious effect has the following composition, g:

| | | |
|---|---|---|
| glycerol | | 21.00 |
| sodium salt of carboxymethylcellulose | | 0.80 |
| sodium benzoate | | 0.18 |
| chalk | | 40.00 |
| carbonate buffer with the pH of 8.9 | | 3.50 |
| silica with a particle size of 5-20 nm and the content of $SiO_2$ of 99.8% | | 1.50 |
| anticarious substance of the following formulation, percent by weight: | | |
| calcium | 2.00 | |
| orthophosphoric acid anion | 1.90 | |
| sodium | 23.00 | |
| magnesium | 0.20 | |
| potassium | 0.18 | |
| mineral acid anion | 10.60 | 0.50 |
| mixture of trace elements | 0.02 | |
| water-soluble proteins | 5.00 | |
| complex citrate compounds as calculated for citric acid anion | 57.0 | |
| saccharin | | 0.04 |
| sodium laurylsulphate | | 1.50 |
| high-purity petroleum oil with kinematic viscosity of $16.5 \times 10^{-6}$ to $23.0 \times 10^{-6}$ at the temperature of 50° C. | | 0.50 |
| flavouring agent | | 0.80 |
| water | | to 100. |

The tooth paste of this composition is prepared following the procedure described in the foregoing Example 1.

The resulting paste has the following properties:

| | |
|---|---|
| dynamic viscosity limit point | 3,700 dyne/cm² |
| plasticity coefficient | 74 |
| foam number | 335 ml |
| foam stability | 0.85. |
| 20% aqueous solution of the paste suspension has pH = 8.9. | |

EXAMPLE 3

A treatment-and-prophylactic tooth paste possessing anticarious effect has the following composition, g:

| | | |
|---|---|---|
| glycerol | | 25.00 |
| sodium salt of carboxymethylcellulose | | 1.40 |
| sodium benzoate | | 0.22 |
| chalk | | 34.00 |
| carbonate buffer with the pH of 8.9 | | 2.50 |
| silica with a particle size of 5-20 nm and the content of $SiO_2$ of 99.8% | | 2.50 |
| anticarious substance having the following formulation, percent by weight: | | |
| calcium | 4.00 | |
| orthophosphoric acid anion | 3.92 | |
| sodium | 21.20 | |
| magnesium | 0.14 | |
| potassium | 0.12 | |
| mineral acid anion | 8.20 | 1.50 |
| mixture of trace elements | 0.02 | |
| water-soluble proteins | 3.00 | |
| complex citrate compounds as calculated for citric acid anion | 59.40 | |
| saccharin | | 0.08 |
| high-purity petroleum oil with kinematic viscosity of $16.5 \times 10^{-6}$ to $23 \times 10^{-6}$ m²/sec at the temperature of 50° C. | | 1.20 |
| sodium laurylsulphate | | 2.50 |
| flavouring substance | | 1.20 |
| water | | to 100. |

The tooth paste of this composition is prepared in a manner similar to that described in Example 1 hereinbefore.

The resulting paste has the following properties:

| | |
|---|---|
| dynamic viscosity limit point | 1,600 dyne/cm² |
| plasticity coefficient | 33 |
| foam number | 350 ml |
| foam stability | 0.90 |
| 20% aqueous solution of the paste suspension has pH of 8.85. | |

EXAMPLE 4

A treatment and-prophylactic paste with anticarious effect has the following composition, g:

| | |
|---|---|
| sodium salt of carboxymethylcellulose | 0.97 |

-continued

| | | |
|---|---|---|
| glycerol | | 20.00 |
| sodium benzoate | | 0.19 |
| anticarious substance having the following formulation, percent by weight: | | |
| calcium | 3.50 | |
| orthophosphoric acid anion | 5.00 | |
| sodium | 20.20 | |
| magnesium | 0.18 | |
| potassium | 0.15 | |
| mineral acid anion | 7.95 | 1.00 |
| mixture of trace elements | 0.02 | |
| water-soluble proteins | 1.10 | |
| complex citrate compounds as calculated for citric acid anion | 61.90 | |
| dicalciumphosphate dihydrate | | 38.00 |
| chalk | | 4.00 |
| sodium laurylsulphate | | 2.50 |
| flavouring substance | | 0.80 |
| water | | up to 100. |

The tooth paste of this composition is prepared in a manner similar to that described in Example 1 hereinbefore.

The resulting tooth paste has the following properties:

| | |
|---|---|
| dynamic viscosity limit point, dyne/cm$^2$ | 3,100 |
| plasticity coefficient | 65 |
| foam number | 350 ml |
| foam stability | 1.0. |
| 20% aqueous solution of the paste suspension has pH of 8.0. | |

EXAMPLE 5

A treatment-and-prophylactic tooth paste possessing anticarious effect has the following composition, g:

| | | |
|---|---|---|
| sodium salt of carboxymethylcellulose | | 1.0 |
| glycerol | | 20.00 |
| sodium benzoate | | 0.20 |
| anticarious substance having the following formulation, percent by weight: | | |
| calcium | 3.20 | |
| orthophosphoric acid anion | 4.90 | |
| sodium | 22.0 | |
| magnesium | 0.18 | |
| potassium | 0.17 | |
| mineral acid anion | 8.95 | 1.50 |
| mixture of trace elements | 0.02 | |
| water-soluble proteins | 1.10 | |
| complex citrate compounds as calculated for citric acid anion | 59.48 | |
| dicalciumphosphate dihydrate | | 36.0 |
| chalk | | 4.20 |
| sodium laurylsulphate | | 2.55 |
| flavouring substance | | 1.00 |
| water | | to 100. |

The tooth paste of this composition is prepared in a manner similar to that described in Example 1.
The resulting paste has the following properties:

| | |
|---|---|
| dynamic viscosity limit point | 3,600 dyne/cm$^2$ |
| plasticity coefficient | 68 |
| foam number | 350 ml |
| foam stability | 0.95 |
| 20% aqueous solution of the paste suspension has pH of 7.9. | |

EXAMPLE 6

A treatment-and-prophylactic tooth paste possessing anticarious effect has the following composition in grams:

| | | |
|---|---|---|
| sodium salt of carboxymethylcellulose | | 1.10 |
| glycerol | | 20.00 |
| sodium benzoate | | 0.21 |
| anticarious substance having the following formulation, percent by weight: | | |
| calcium | 3.80 | |
| orthophosphoric acid anion | 5.00 | |
| sodium | 22.80 | |
| magnesium | 0.20 | |
| potassium | 0.18 | |
| mineral acid anion | 8.88 | 2.00 |
| mixture of trace elements | 0.02 | |
| water-soluble proteins | 1.36 | |
| complex citrate compounds as calculated for citric acid anion | 57.76 | |
| dicalciumphosphate dihydrate | | 34.00 |
| chalk | | 4.50 |
| sodium laurylsulphate | | 2.60 |
| flavouring agent | | 1.20 |
| water | | to 100. |

The paste of this composition is prepared in a manner similar to that described in Example 1 hereinbefore.
The resulting paste has the following properties:

| | |
|---|---|
| dynamic viscosity limit point | 3,900 dyne/cm$^2$ |
| plasticity coefficient | 72 |
| foam number | 348 ml |
| foam stability | 0.95 |
| 20% aqueous solution of the paste suspension has pH of 8.0. | |

What is claimed is:

1. A treatment-and-prophylactic tooth paste possessing an abrasive agent, a gelating agent, a wetting agent, a surfactant, a flavouring agent, 0.5 to 2% by weight of a substance possessing anticaries effect comprising a product obtained by treatment of a bone tissue with a diluted mineral acid till a complete dissolution of mineral components and water-soluble proteins contained in the bone tissue, separation of the resulting solution, dilution thereof with water with the addition of citric acid or salts thereof as a stabilizing agent, followed by neutralization of the solution and drying and containing the following components, percent by weight:

| | |
|---|---|
| calcium | 2 to 6 |
| sodium | 19 to 23 |
| potassium | 0.04 to 0.18 |
| mineral acid anion | 6 to 10.6 |
| orthophosphoric acid anion | 1.5 to 5.0 |
| water-soluble proteins | 1.0 to 5.0 |
| magnesium | 0.05 to 0.2 |
| a mixture of trace elements including fluorine, manganese, tin, zinc, iron | 0.01 to 0.02 |
| complex citrate compounds as calculated for citric acid anion | the balance. |

2. A treatment-and-prophylactic tooth paste possessing anticaries effect as claimed in claim 1, also containing a preservative and consisting of the following components,

| | |
|---|---|
| abrasive agent | 34 to 42.5 |

-continued

| | |
|---|---|
| gelating agent | 19 to 25 |
| wetting agent | 0.8 to 1.4 |
| surfactant | 1.5 to 2.6. |
| preservative | 0.18 to 0.22 |
| flavouring agent | 0.8 to 1.2 |
| anticaries substance | 0.5 to 2.0 |
| water | the balance. |

3. A treatment-and-prophylactic tooth paste possessing anticaries effect according to claim 1 consisting of the following components, percent by weight:

| | |
|---|---|
| sodium salt of carboxymethylcellulose | 0.97 to 1.10 |
| glycerol | 19.00 to 21.00 |
| sodium benzoate | 0.19 to 0.21 |
| anticaries substance | 1.00 to 2.00 |
| dicalcium phosphate dihydrate | 34.00 to 38.00 |
| chalk | 4.00 to 4.50 |
| sodium laurylsulphate | 2.50 to 2.60 |
| flavouring agent | 0.80 to 1.20 |
| water | the balance. |

4. A treatment-and-prophylactic tooth paste possessing anticaries effect according to claim 2, additionally containing a purified petroleum oil with a kinematic viscosity of from $16.5 \times 10^{-6}$ to $23.0 \times 10^{-6}$ m$^2$/sec at the temperature of 50° C., a buffer solution with pH of 8 to 10 and silica with a particle size of 5 to 20 nm and the content of SiO$_2$ of 99.8% at the following proportions of the components, percent by weight:

| | |
|---|---|
| chalk | 34 to 40 |
| glycerol | 21 to 25 |
| sodium salt of carboxymethylcellulose | 0.8 to 1.4 |
| high-purity petroleum oil (with kinematic viscosity of $16.5 \times 10^{-6}$ to $23.0 \times 10^{-6}$ m$^2$/sec at the temperature of 50° C.) | 0.5 to 1.5 |
| sodium laurylsulphate | 1.5 to 2.5 |
| sodium benzoate | 0.18 to 0.22 |
| saccharin | 0.04 to 0.08 |
| flavouring substance | 0.8 to 1.2 |
| buffer solution with a pH of 8 to 10 | 2.5 to 3.5 |
| silica with a particle size of 5 to 20 nm and SiO$_2$ content of 99.8% | 1.5 to 2.5 |
| anticaries substance | 0.5 to 1.5. |
| water | the balance. |

* * * * *